United States Patent [19]

Ennis et al.

[11] Patent Number: 5,077,073

[45] Date of Patent: Dec. 31, 1991

[54] ETHOXYLATED SUGAR AND SUGAR ALCOHOL ESTERS USEFUL AS FAT SUBSTITUTES

[75] Inventors: John L. Ennis, Arlington; Peter W. Kopf, Sudbury; John R. Powell, Brookline; Stephen E. Rudolph, Carlisle; Martin F. van Buren, Chelmsford, all of Mass.

[73] Assignee: The Proctor & Gamble Company, Cincinnati, Ohio

[21] Appl. No.: 398,216

[22] Filed: Aug. 25, 1989

[51] Int. Cl.$^5$ .................. C07H 15/04; A23L 1/00; A23L 1/29
[52] U.S. Cl. .......................... 426/531; 426/601; 426/607; 426/611; 426/804; 536/116; 536/120
[58] Field of Search .............. 426/531, 601, 607, 611, 426/804; 536/120, 116

[56] References Cited

U.S. PATENT DOCUMENTS

| | | | |
|---|---|---|---|
| 3,317,508 | 5/1967 | Winquist, Jr. et al. | |
| 3,346,557 | 10/1967 | Patton, Jr. et al. | |
| 3,600,186 | 8/1971 | Mattson et al. | |
| 4,239,907 | 12/1980 | Bedoit, Jr. | 536/120 |
| 4,332,936 | 6/1982 | Nodelman | 536/120 |
| 4,849,242 | 7/1989 | Kershner | 426/601 |
| 4,861,613 | 8/1989 | White et al. | 426/611 |

FOREIGN PATENT DOCUMENTS 52-62216  5/1977  Japan .

OTHER PUBLICATIONS

Chung et al, "Sucrose Monoesters and Diesters in Breadmaking", 1980 Cereal Chemistry vol. 58, pp. 164–170.

Harrigan et al. "Fat Substitutes: Sucrose Esters and Simplease", Cereal Foods World vol. 34, No. 3, pp. 261–267.

The National Institutes of Health Consensus Development ("NIHCD") Conference, Lowering Blood Cholesterol to Prevent Heart Disease, *JAMA*, vol. 253, No. 14, pp. 2080–2086 (1985).

Haumann, "Getting the Fat Out", *JAOCS*, vol. 63, No. 3, pp. 278–288 (Mar. 1986).

LaBarge, "The Search for a Low-Caloric Oil", *Food Technology*, pp. 84–90 (Jan. 1988).

*Primary Examiner*—Donald E. Czaja
*Assistant Examiner*—Evan Federman
*Attorney, Agent, or Firm*—Gary M. Sutter; John M. Howell; Richard C. Witte

[57] ABSTRACT

The present invention relates to a fat substitute comprising an ethoxyloted sugar or sugar alcohol sucrose fatty acid ester. Between 1 and about 50 alkoxyl groups are attached by ether linkages to each polyol molecule. Each ethoxylated polyol is esterified with between about 6 and about 8 fatty acid groups, the fatty acids containing between about 2 and about 24 carbon atoms. The invention also relates to a low calorie fat-containing food composition which comprises: (a) non-fat ingredients; and (b) fat ingredients, from about 10% to about 100% by weight of said fat ingredients consisting essentially of the above-described fat substitute.

12 Claims, No Drawings

ETHOXYLATED SUGAR AND SUGAR ALCOHOL ESTERS USEFUL AS FAT SUBSTITUTES

TECHNICAL FIELD

The present invention relates to the field of low calorie fat and oil substitutes. Specifically, the invention relates to fatty acid polyesters of alkoxylated sugars and sugar alcohols. The alkoxyl groups are derived from cyclic ethers containing 2 to 4 carbon atoms, particularly epoxides. The compounds of the invention have been found to be useful for replacing triglyceride fats in low calorie fat-containing food compositions.

BACKGROUND OF THE INVENTION

The consumption of large amounts of triglyceride fats has been linked to various health problems. For example, one of the most common metabolic problems among people today is obesity. This condition is primarily due to ingestion of a greater number of calories than are expended. Fat is the most concentrated form of energy in the diet, with each gram of fat supplying approximately nine calories, and triglyceride fats constitute about 90% of the total fat consumed in the average diet.

The National Institutes of Health Consensus Development Conference, "Lowering Blood Cholesterol to Prevent Heart Disease," JAMA, Vol. 253, No. 14, pp. 2080–2086 (1985), concluded that elevation of blood cholesterol levels is a major cause of coronary artery disease, and recommended a reduction in the amount of fat eaten to reduce blood serum cholesterol levels.

Hence, there is a need for ways to reduce the amount of triglyceride fats in the diet, in order to reduce the health risks associated with these fats.

Numerous fat substitutes are known to the art. A review of some of the approaches tried for replacing fats and oils is given in an article by Haumann, "Getting the Fat Out," JAOCS, Vol. 63, No. 3, pp. 278–288 (March 1986). Various approaches and products that have been suggested for replacement of the fat content of foods are examined in LaBarge, "The Search for a Low-Caloric Oil," Food Technology, pp. 84–90 (January 1988).

A partial list of some of the reduced calorie fat substitutes known to the art includes the following: fatty alcohol esters of polycarboxylic acids (U.S. Pat. No. 4,508,746 to Hamm, issued Apr. 2, 1985); fatty polyethers of polyglycerol (U.S. Pat. No. 3,932,532 to Hunter et al., issued Jan. 13, 1976) (food use disclosed in German Patent 207,070, issued February 15, 1984); ethers and ether-esters of polyols containing the neopentyl moiety (U.S. Pat. No. 2,962,419 to Minich, issued Nov. 29, 1960); fatty alcohol diesters of dicarboxylic acids such as malonic and succinic acid (U.S. Pat. No. 4,582,927 to Fulcher, issued Apr. 15, 1986); triglyceride esters of alpha branched chain-alkyl carboxylic acids (U.S. Pat. No. 3,579,548 to Whyte, issued May 18, 1971); fatty acid diglyceride, diesters of dibasic acids (U.S. Pat. No. 2,874,175 to Feuge et al.); polyorganosiloxanes (European Patent Application 205,273 to Frye); alpha-acylated glycerides (U.S. Pat. No. 4,582,715 to Volpenhein); medium chain triglycerides; highly esterified polyglycerol esters; acetin fats; plant sterol esters; N-Oil; polyoxyethylene esters; jojoba esters; mono/diglycerides of fatty acids; and mono/diglycerides of short-chain dibasic acids.

Sugar and sugar alcohol fatty acid polyesters are disclosed for use as fat substitutes in U.S. Pat. No. 3,600,186 to Mattson et al., issued Aug. 17, 1971. However, there is no suggestion that alkoxylated sugar and sugar alcohol polyesters are also suitable as fat substitutes.

Alkoxylated sugars and sugar alcohols are known to the art for use in making urethanes and polyurethanes. For example, U.S. Pat. No. 4,332,936 to Nodelman, issued June 1, 1982, discloses an improved method for making oxyalkylated polyols (including certain sugars and sugar alcohols) by adding a solid initiator to the reaction mixture. The products are said to be particularly suited for the production of rigid polyurethane foams. U.S. Pat. No. 3,317,508 to Winquist, Jr. et al., issued May 2, 1967, discloses a process for making alkylene oxide adducts of polyhydroxy organic compounds (including sugars) by utilizing novel ditertiary amino catalysts.

U.S. Pat. No. 4,239,907 to Bedoit, Jr., issued Dec. 16, 1980, discloses the employment of a water-soluble initiator to make alkoxylated sucrose and sorbitol. The product is said to be useful in the production of urethane foams. U.S. Pat. No. 3,346,557 to Patton, Jr., et al., issued Oct. 10, 1967, discloses another method for oxyalkylating polyols. While the above-mentioned Nodelman, Winquist, Bedoit, and Patton patents disclose alkoxylated sugars and sugar alcohols, they do not disclose the fatty acid esters of these compounds.

Japanese Kokai Patent No. Sho 52[1977]-62216 to Nakamura et al., published May 23, 1977, discloses polyoxyalkylenated sucrose that is esterified with aliphatic acids having $C_8$ to $C_{22}$ saturated or unsaturated alkyl groups. However, the sucrose esters contain only 1 to 3 acid groups per sucrose molecule. The polyoxyalkylenated sucrose esters are said to be useful as nonionic surfactants.

One of the main problems in attempting to formulate fat compounds that have decreased absorbability and thus low calorie properties is to maintain the desirable and conventional physical properties of edible fat. Thus, to be a practical low calorie fat, a compound must resemble conventional triglyceride fat, and have the same utility in various fat-containing food compositions such as shortening, margarine, cake mixes, and the like, and be useful in frying or baking.

None of the above-mentioned references suggests that fatty acid polyesters of alkoxylated sugars and sugar alcohols are particularly suitable as low calorie fat substitutes for use in fat-containing food compositions. Alkoxylated sugars and sugar alcohols are known for making urethane foams, but there is no suggestion in the art of fatty acid esters of these compounds being suitable as fat substitutes. These compounds have now surprisingly been found to have organoleptic and other physical properties that make them well-suited as fat substitutes. This is surprising in view of the significant structural difference between the present compounds and sugar and sugar alcohol esters or triglycerides.

Moreover, the compounds of the invention have now been found to be resistant to hydrolysis and therefore nondigestible. Accordingly, the compounds contain zero calories, in contrast to the nine calories per gram in triglyceride fats.

It is, therefore, an object of the present invention to provide fat substitutes comprising fatty acid polyesters of alkoxylated sugars and sugar alcohols.

It is another object of the present invention to provide fat substitutes that are resistant to hydrolysis and therefore nondigestible and noncaloric.

It is a further object of the present invention to provide low calorie fat-containing food compositions containing these fat substitutes.

These and other objects of the present invention will become evident from the disclosure herein.

All parts, percentages and ratios used herein are by weight unless otherwise indicated.

SUMMARY OF THE INVENTION

The present invention relates to a fat substitute comprising a fatty acid ester of an alkoxylated polyol, where the polyol is a sugar or sugar alcohol. Between about 1 and about 50 alkoxyl groups are attached by ether linkages to each polyol molecule. Each alkoxylated polyol is esterified with between about 6 and about 8 fatty acid groups, the fatty acids containing between about 2 and about 24 carbon atoms. The alkoxyl groups are derived from cyclic ethers selected from propylene oxide, ethylene oxide, 1-butene oxide, cis-2-butene oxide, trans-2-butene oxide, 1-hexene oxide, tertbutylethylene oxide, cyclohexene oxide, 1-octene oxide, cyclohexylethylene oxide, styrene oxide, 1-decene oxide, 1-octadecene oxide, isobutylene oxide, epichlorohydrin, epibromohydrin, epiiodohydrin, perfluoropropylene oxide, cyclopentene oxide, 1-pentene oxide, oxetane, oxetane derivatives, and mixtures thereof. The invention also relates to a low calorie fat-containing food composition which comprises: (a) non-fat ingredients; and (b) fat ingredients, from about 10% to about 100% by weight of said fat ingredients consisting essentially of the above-described fat substitute.

DETAILED DESCRIPTION OF THE INVENTION

The present invention relates to certain fatty acid polyesters of alkoxylated sugars and sugar alcohols which have now been surprisingly discovered to be useful as fat substitutes, particularly for use in low calorie fat-containing food compositions. The food compositions comprise: (a) non-fat ingredients; and (b) fat ingredients, from about 10% to 100% by weight of the fat ingredients consisting essentially of the alkoxylated sugar or sugar alcohol polyesters of the present invention.

The compounds of the present invention (and fat-containing food compositions containing these compounds) have desirable physical properties and palatability compared to ordinary triglyceride fats and compositions containing same. However, these compounds have a substantially lower effective caloric value than triglyceride fats (zero calories/gram versus nine calories/gram) because they are not digested or absorbed in the intestinal tract.

A. Definitions

By "alkoxylated" sugars and sugar alcohols, as used herein, is meant that the sugars and sugar alcohols are reacted with cyclic ether compounds selected from the group consisting of propylene oxide, ethylene oxide, 1-butene oxide, cis-2-butene oxide, trans-2-butene oxide, 1-hexene oxide, tert-butylethylene oxide, cyclohexene oxide, 1-octene oxide, cyclohexylethylene oxide, styrene oxide, 1-decene oxide, 1-octadecene oxide, isobutylene oxide, epichlorohydrin, epibromohydrin, epiiodohydrin, perfluoropropylene oxide, cyclopentene oxide, 1-pentene oxide, oxetane, oxetane derivatives, and mixtures thereof, to form hydroxyl terminated ether compounds. With the exception of oxetane and oxetane derivatives, these compounds are all epoxides. The ring structures of the compounds contain 2 to 4 carbon atoms and an oxygen atom. Preferred compounds for use herein are propylene oxide, ethylene oxide, and mixtures thereof. Most preferred is propylene oxide. These compounds and their chemistry are known to those skilled in the art. See, e.g., Encyclopedia of Polymer Science and Technology, 1st Ed., Vol. 6, 1,2-Epoxide Polymers, pp. 108, 154, 186, 187, and 192, Interscience Publishers, New York (1967), and 2nd Ed., Vol. 6, pp. 276-277 (1985); and Frisch, Cyclic Monomers. Vol. XXVI of the High Polymers Series, pp. 8-9, 54-59 and 100-102, Wiley-Interscience, New York (1972).

By "alkoxyl groups", as used herein, is meant the cyclic ether compounds disclosed above after they have reacted with and become attached to a sugar or sugar alcohol through ether linkages. For example, propylene oxide reacts with sucrose to form propoxylated sucrose; the propylene oxide changes into a "propoxyl" group during the reaction. Similarly, ethylene oxide becomes an "ethoxyl" group. Hence, the alkoxyl groups are "derived from" the above-mentioned cyclic ether compounds. This is understood in the art; see, e.g., U.S. Pat. No. 4,264,478 of Seldner, issued Apr. 28, 1981, column 3, lines 31-43 (incorporated by reference herein).

By "polyol", as used herein, is meant a sugar or sugar alcohol, or mixtures thereof. The term "sugar" is used herein in its conventional sense as generic to mono- and disaccharides. The term "sugar alcohol" is also used in its conventional sense as generic to the reduction product of sugars wherein the aldehyde or ketone group has been reduced to an alcohol. Suitable for use in the present invention are sugars and sugar alcohols containing at least 4 hydroxyl groups. The fatty acid ester compounds of the invention are prepared by reacting an alkoxylated monosaccharide, disaccharide or sugar alcohol with fatty acids as discussed below.

Examples of suitable monosaccharides are those containing 4 hydroxyl groups such as xylose, arabinose, and ribose; the sugar alcohol derived from xylose, i.e., xylitol, is also suitable. The monosaccharide erythrose is not suitable for the practice of this invention since it only contains 3 hydroxyl groups; however, the sugar alcohol derived from erythrose, i.e., erythritol, contains 4 hydroxyl groups and is thus suitable. Among 5 hydroxyl-containing monosaccharides that are suitable for use herein are glucose, mannose, galactose, fructose, and sorbose. A sugar alcohol derived from sucrose, glucose, or sorbose, e.g., sorbitol, contains 6 hydroxyl groups and is also suitable as the alcohol moiety of the fatty acid ester compound. Examples of suitable disaccharides are maltose, lactose, and sucrose, all of which contain 8 hydroxyl groups. Sucrose is especially preferred.

B. Fatty Acid Polyesters of Alkoxylated Sugars and Sugar Alcohols

A fat substitute according to the present invention comprises a fatty acid ester of an alkoxylated polyol, wherein:

(a) the polyol is selected from the group consisting of sugars and sugar alcohols, and mixtures thereof, wherein the sugars and sugar alcohols contain at least 4 hydroxyl groups;

(b) between 1 and about 50 alkoxyl groups are attached by ether linkages to each polyol molecule;
(c) each alkoxylated polyol is esterified with between about 6 and about 8 fatty acid groups;
(d) the fatty acids contain between about 2 and about 24 carbon atoms; and
(e) the alkoxyl groups are derived from cyclic ethers selected from the group consisting of propylene oxide, ethylene oxide, 1-butene oxide, cis-2-butene oxide, trans-2-butene oxide, 1-hexene oxide, tert-butylethylene oxide, cyclohexene oxide, 1-octene oxide, cyclohexylethylene oxide, styrene oxide, 1-decene oxide, 1-octadecene oxide, isobutylene oxide, epichlorohydrin, epibromohydrin, epiiodohydrin, perfluoropropylene oxide, cyclopentene oxide, 1-pentene oxide, oxetane, oxetane derivatives, and mixtures thereof.

It has been discovered that each sugar or sugar alcohol group of the fat substitute must have attached to it through ether linkages between 1 and about 50 alkoxyl groups. Polyesters with higher degrees of alkoxylation will have more polyether character than is desirable in a fat substitute. The compounds contain at least one alkoxyl group; it is hypothesized that an alkoxylated structure may have even more resistance to hydrolysis (to an unexpectedly greater extent) than unalkoxylated sugar and sugar alcohol esters because placing the ester linkage farther away from the polyol makes it more difficult for lipase enzymes to handle these compounds and initiate digestion. Preferably, between about 8 and about 2 alkoxyl groups are attached to each polyol molecule, more preferably between about 8 and about 16.

Moreover, attachment of fatty acid ester groups at the ends of the alkoxyl groups produces a large hydrophilic center in the compounds. As a result, it is believed that the compounds form better emulsions in the gut and thus are more compatible with the gastrointestinal tract so that fewer GI problems such as oil separation will occur.

As is well known to the art, sugars and sugar alcohols contain varying numbers of attachment sites available for ether linkages with alkoxyl groups depending on their number of hydroxyl groups; for example, sucrose has eight attachment sites corresponding to its eight hydroxyl groups. Preferably, the number of alkoxyl groups attached by ether linkages to each attachment site of the sugar or sugar alcohol varies between about 1 and about 4, more preferably between about 1 and about 2. When more than one alkoxyl group attaches to a single attachment site of the sugar or sugar alcohol, the alkoxyl groups are polymerized in the form of a chain. The chemistry of polymerization of alkoxyl groups is known to those skilled in the art. See, e.g., Frisch, Cyclic Monomers, Vol. XXVI of High Polymers Series, Wiley Interscience, New York, pp. 36–39 (1972); and Saunders and Frisch, Polyurethanes: Chemistry and Technology, Part I, Interscience Publishers, New York, pp. 32–43 (1962).

The fatty acid groups of the present fat substitute are esterified to the alkoxylated sugar or sugar alcohol. Each alkoxylated polyol is esterified with between about 6 and about 8 fatty acid groups. Fatty acid esters of alkoxylated polyols with esterification less than six will begin to have surfactant-type properties making them unsuitable as fat substitutes. Complete esterification is more desirable to attain the desired organoleptic character in the alkoxylated sugar or sugar alcohol polyester. Accordingly, it is preferred that each alkoxylated polyol is esterified with about 8 fatty acid groups.

The fatty acids are $C_2$ to $C_{24}$ in carbon chain length to impart the desired organoleptic character to the polyester compounds. Preferred fatty acids are $C_8$ to $C_{22}$, more preferred are $C_{14}$ to $C_{18}$, and most preferred are $C_{18}$. Examples of such fatty acids include acetic, butyric, caprylic, capric, lauric, myristic, myristoleic, palmitic, palmitoleic, stearic, oleic, ricinoleic, linoleic, linolenic, eleostearic, arachidic, arachidonic, behenic, and erucic acid. The fatty acids can be derived from naturally occurring or synthetic fatty acids, and can be saturated or unsaturated, including positional or geometrical isomers (e.g., cis and trans isomers). Oleic acid is especially preferred, and stearic acid second most preferred.

C. Methods for Making the Fatty Acid Polyesters of Alkoxylated Sugars and Sugar Alcohols For making the fat substitutes of the present invention, the starting material is an alkoxylated sugar or sugar alcohol. Union Carbide Corporation, Danbury, Conn., sells propoxylated sucrose under the trade name Niax ® E-651 polyol. This compound is prepared by reacting 1 mole of sucrose with 14 moles of propylene oxide to form a propoxylated sucrose. A process for making propoxylated sucrose and other alkylene oxide adducts of polyhydroxy organic compounds is disclosed in U.S. Pat. No. 3,317,508 assigned to Union Carbide Corp., issued May 2, 1967 (incorporated by reference herein); see, specifically, Example 1. The following patents (all incorporated by reference herein) also disclose methods for making various alkoxylated sugars and sugar alcohols: U.S. Pat. No. 4,332,936 to Nodelman, issued June 1, 1982; U.S. Pat. No. 4,239,907 to Bedoit, Jr., issued Dec. 16, 1980; and U.S. Pat. No. 3,346,557 to Patton, Jr. et al., issued Oct. 10, 1967.

The alkoxylated sugar or sugar alcohol is esterified with fatty acids by any of a variety of general esterification methods well known to those skilled in the art. These methods include: acylation with a fatty acid chloride, acylation with a fatty acid anhydride, acylation with a fatty acid per se, and transesterification with another ester such as methyl, ethyl or glycerol. The preferred method is acylation with a fatty acid chloride, as disclosed in Example 1 hereinafter.

Example 1 shows the preparation of a propoxylated sucrose octaoleate Niax ® E-651 (34.1 grams) is first diluted in a solvent mixture of 50 ml DMF and 100 ml pyridine. While this DMF/pyridine mixture is the preferred solvent, it is anticipated that other organic solvents known to those skilled in the art could also be used. This solution is charged to a flask equipped with a reflux condenser, dry $N_2$ purge, and a magnetic stirrer.

The Niax ® E-651 solution is heated to a temperature between 40° C. (104° F.) and 45° C. (113° F.) while the flask is purged with nitrogen. While 40°–45° C. (104°–113° F.) is the preferred temperature range, the practical operating range can vary from 0° C. (32° F.) to the solvent reflux temperature; the upper limit will vary with the solvent composition (it is about 115° C. (239° F.) for the DMF/pyridine solvent). The reaction is preferably conducted under nitrogen. However, other inert gases can be used instead of nitrogen, such as helium or argon.

Separately, oleoyl chloride (72.5 grams) is diluted in 200 ml of methylene chloride. Chlorides of other fatty acids besides oleic acid are also suitable for use in the present invention, but oleic acid is the most preferred fatty acid while stearic acid is second most preferred. Other suitable $C_2$ to $C_{24}$ fatty acids are described hereinabove. The preferred solvent for the fatty acid chloride is methylene chloride, but other suitable solvents can be used that are known to those skilled in the art.

The mole ratio of oleoyl chloride to propoxylated sucrose can range between about 8.0 and about 8.8, preferably between about 8.2 and about 8.6.

The oleoyl chloride solution is added dropwise to the stirred, heated Niax®solution under nitrogen, over a period of about 1.5 hours. The time for addition can vary between about 1 hour and about 3 hours.

After completion of the addition, the reactants are heated to 55° C. (131° F.) and reacted for 20 hours. The reaction temperature can vary between about 45° C. (113° F.) and the solvent reflux temperature (about 59° C. (138° F.) in this example). The reaction time is between about 16 hours and about 48 hours, preferably between about 20 hours and about 26 hours.

After the reaction is complete, the reactants are cooled to about room temperature and stirred under nitrogen for about 16 hours (can vary between about 1 hour and about 20 hours).

The product is isolated by any suitable method known to the art. Example 1 hereinbelow discloses details of the preferred method for isolating a propoxylated sucrose octaoleate according to the invention.

D. Resistance of the Present Alkoxylated Sugar and Sugar Alcohol Polyesters to Hydrolysis The propoxylated sucrose polyester product of Example 1 hereinbelow is measured for resistance to hydrolysis by two techniques: (1) a 30-minute digest with commercial porcine lipase, and (2) a pH stat hydrolysis rate measurement with rat pancreatic juice.

(1) Digest with Steapsin

The initial screening of this product is performed with steapsin, a porcine pancreatic lipase, in a digest medium of Tris buffer, pH 8.0. The substrate (propoxylated sucrose polyester), medium, and enzyme are emulsified by vigorous shaking on a wrist-action shaker for thirty minutes at room temperature. The measurement of hydrolysis is by titration with a standardized base solution using phenophthalein indicator. The free fatty acid released by enzyme is the equivalent of the base consumed in the titration and is expressed as a percent of the total fatty acid initially present in the product. The data presented in Table I are the result of initial stability testing with steapsin. The data suggest that little or no hydrolysis occurs in the presence of the porcine lipase. (There is no titration for the presence of free acid in the samples prior to digestion by lipase, and the apparent low percent hydrolysis could be even lower if this assessment is made.)

TABLE I

| | | Percent Hydrolysis with Commerical Lipase | | | | | | |
|---|---|---|---|---|---|---|---|---|
| Product | M. W. (gm/mol) | Fat (mg) | Fat (umol) | F. A. (umol) | KOH (ml) | KOH (umol) | F.F.A. (umol) | % Hydrolysis of Ester Bonds |
| Example 1 | 3654 | 522 | 143 | — | 0.05 | 5 | 5 | 0.3 |
| Crisco Oil | 885 | 654 | 738 | 2216 | 14.20 | 1346 | 1346 | 60.7 |

(2) pH Stat Measurement with Pancreatic Juice

The in vitro lipolysis of the product of Example 1 is examined using a pH Stat recording titrator. A nominal 1 gram of the product (substrate) is added to 70 ml of histidine buffer medium containing 1 ml of a 1% sodium taurocholate solution. The medium is emulsified in a 100 ml 4-neck roundbottom flask by vigorous shaking with a wrist-action shaker for 10 minutes. The flask is then fitted with pH electrode, titrant delivery tube, and propeller stirrer. The reaction is initiated by delivery of 1.0 ml of enzyme (bile-pancreatic combination fluid) into the stirred emulsion. The pH is maintained at 9.0 by the addition of 0.1 N KOH delivered from a Metrohm pH stat-titrator system. The linear portion of the plot resulting from added base versus time during the first 1-4 minutes of the reaction is used to determine the rate of fatty acid production for the product.

The digestibility of the product is shown in Table II. In contrast to the porcine lipase, the bile-pancreatic combination fluid contains nonspecific lipase which would hydrolyze both primary and secondary esters and, therefore, might potentially hydrolyze any ester bond in the product. Evidence for the activity of nonspecific lipase in the combination fluid is seen in the hydrolysis tracing of the product. The assessment of hydrolytic stability by pH-stat tracing essentially confirms the preliminary findings with porcine pancreatic lipase.

TABLE II

| Product | Sample Wt. (gm) | Rate of Hydrolysis (ueq KOH/min) |
|---|---|---|
| Example 1 | 1.0011 | 0.0 |

E. Low Calorie Fat-Containing Food Compositions

The alkoxylated sugar and sugar alcohol polyesters of the present invention can be used as partial or total replacements for normal triglyceride fats in any fat-containing food composition to provide low calorie benefits. The amount of the present compounds included in the fat will depend upon the food composition and the low calorie effect desired. In order to obtain a significant low calorie effect, it is necessary that at least about 10% of the fat in the food composition comprise the present compounds. On the other hand, very low calorie and thus highly desirable food compositions of the present invention are obtained when the fat comprises up to 100% of the present compounds.

The compounds of the present invention are useful in a wide variety of food and beverage products. For example, the compounds can be used in the production of baked goods in any form, such as mixes, shelf-stable baked goods, and frozen baked goods. Possible applications include, but are not limited to, cakes, brownies, muffins, bar cookies, wafers, biscuits, pastries, pies, pie crusts, and cookies, including sandwich cookies and chocolate chip cookies, particularly the storage-stable dual-textured cookies described in U.S. Pat. No. 4,455,333 of Hong & Brabbs. The baked goods can contain fruit, cream, or other fillings. Other baked good uses include breads and rolls, crackers, pretzels, pancakes, waffles, ice cream cones and cups, yeast-raised baked goods, pizzas and pizza crusts, baked farinaceous snack foods and other baked salted snacks.

In addition to their uses in baked goods, the present compounds can be used alone or in combination with other regular, reduced calorie or zero calorie fats to make shortening and oil products. The other fats can be synthetic or derived from animal or vegetable sources, or combinations of these. Shortening and oil products include, but are not limited to, shortenings, margarines, spreads, butter blends, lards, cooking and frying oils, salad oils, popcorn oils, salad dressings, mayonnaise, and other edible oils. The present compounds can be used to make foods that are fried in oil (e.g., Pringle's potato chips, corn chips, tortilla chips, other fried farinaceous snack foods, French fries, doughnuts, and fried chicken).

Imitation dairy products can also be made (e.g., butter, ice cream and other fat-containing frozen desserts, yogurt, and cheeses, including natural cheeses, processed cheeses, cream cheese, cottage cheese, cheese foods and cheese spread, milk, cream, sour cream, butter milk, and coffee creamer).

The present compounds are also useful for making meat products (e.g, hamburgers, hot dogs, frankfurters, wieners, sausages, bologna and other luncheon meats, canned meats, including pasta/meat products, stews, sandwich spreads, and canned fish), meat analogs, tofu, and various kinds of protein spreads.

Sweet goods and confections can also be made (e.g., candies, chocolates, chocolate confections, frostings and icings, syrups, cream fillings, and fruit fillings), as well as nut butters and various kinds of soups, dips, sauces and gravies.

The present compounds can also be fortified with vitamins and minerals, particularly the fat-soluble vitamins. The fat-soluble vitamins include vitamin A, vitamin D, vitamin E, and vitamin K. The amount of the fat-soluble vitamins employed herein to fortify the present compounds can vary. If desired, the compounds can be fortified with a recommended daily allowance (RDA), or increment or multiple of an RDA, of any of the fat-soluble vitamins or combinations thereof.

The present compounds are particularly useful in combination with particular classes of food and beverage ingredients. For example, an extra calorie reduction benefit is achieved when the compounds are used with noncaloric or reduced calorie sweeteners alone or in combination with bulking agents. Noncaloric or reduced calorie sweeteners include, but are not limited to, aspartame; saccharin; alitame, thaumatin; dihydrochalcones; cyclamates; steviosides; glycyrrhizins, synthetic alkoxy aromatics, such as Dulcin and P-4000; sucrolose; suosan; miraculin; monellin; sorbitol; xylitol; talin; cyclohexylsulfamates; substituted imidazolines; synthetic sulfamic acids such as acesulfame, acesulfam-K and n-substituted sulfamic acids; oximes such as perilartine; rebaudioside-A; peptides such as aspartyl malonates and succanilic acids; dipeptides; amino acid based sweeteners such as gem-diaminoalkanes, meta-aminobenzoic acid, L-aminodicarboxylic acid alkanes, and amides of certain alpha-aminodicarboxylic acids and gem-diamines; and 3-hydroxy-4-alkyloxyphenyl aliphatic carboxylates or heterocyclic aromatic carboxylates.

The compounds of the present invention can be used in combination with other noncaloric or reduced calorie fats, such as sugar or sugar alcohol fatty acid polyesters, branched chain fatty acid triglycerides, triglycerol ethers, polycarboxylic acid esters, sucrose polyethers, neopentyl alcohol esters, silicone oils/siloxanes, and dicarboxylic acid esters. Other partial fat replacements useful in combination with the present compounds are medium chain triglycerides, highly esterified polyglycerol esters, acetin fats, plant sterol esters, polyoxyethylene esters, jojoba esters, mono/diglycerides of fatty acids, and mono/diglycerides of short-chain dibasic acids.

Bulking or bodying agents are useful in combination with the present compounds in many foods or beverages. The bulking agents can be nondigestible carbohydrates, for example, polydextrose and cellulose or cellulose derivatives, such as carboyxmethylcellulose, carboxyethylcellulose, hydroxypropylcellulose, methylcellulose and microcrystalline cellulose. Other suitable bulking agents include gums (hydrocolloids), starches, dextrins, fermented whey, tofu, maltodextrins, polyols, including sugar alcohols, e.g., sorbitol and mannitol, and carbohydrates, e.g., lactose.

Similarly, foods and beverages can be made that combine the present compounds with dietary fibers to achieve the combined benefits of each. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose, or cellulose flour, can also be used. Naturally occurring fibers include fiber from whole citrus peel, citrus albedo, sugar beets, citrus pulp and vesicle solids, apples, apricots, and watermelon rinds.

Many benefits are obtained from the use of the present compounds in foods and beverages, either when used alone or in combination with the ingredients discussed above. A primary benefit is the calorie reduction achieved when the present compounds are used as a total or partial fat replacement. This calorie reduction can be increased by using combinations of the present compounds with reduced calorie sweeteners, bulking agents, or other reduced calorie or noncaloric fats. Another benefit which follows from this use is a decrease in the total amount of triglyceride fats in the diet.

This discussion of the uses, combinations, and benefits of the present compounds is not intended to be limiting or all-inclusive. It is contemplated that other similar uses and benefits can be found that will fall within the spirit and scope of this invention.

The following example is intended only to further illustrate the invention and is not intended to limit the scope of the invention which is defined by the claims.

EXAMPLE 1

(a) Preparation of a fatty acid polyester of propoxylated sucrose

A propoxylated sucrose polyester according to the invention is prepared as follows. The starting material is Niax ® E-651 polyol, a sucrose which has been reacted with 14 moles of propylene oxide to form a propoxylated sucrose and which, therefore, has eight secondary hydroxyl groups available for reaction with fatty acid chlorides. Niax ® E-651 (34.1 g., 0.027 mole) (Union Carbide, Danbury, Conn.) is diluted in DMF (50 ml)/pyridine (100 ml). This solution is charged to a 1 liter, 3-neck round-bottom flask equipped with a reflux condenser, 300 ml cylindrical pressure equalizing addition funnel, thermometer, dry N2 purge and magnetic stirrer. Oleoyl chloride (72.5 g., 0.24 mole) is diluted in methylene chloride (200 ml) and the solution placed in the funnel. The reactor's contents are warmed to 40°–45° C. (104°–113° F.) and the system purged with dry N2. The oleoyl chloride solution is added dropwise to the stirred contents of the reactor over 1.5 hours. A precipitate of pyridine hydrochloride forms halfway through the addition. After completion of the addition, the reactants are heated to 55° C. and held at that temperature for 20 hours. They are then cooled to room temperature and stirred under N2 for an additional 16 hours.

At this point the reaction mixture is transferred to a 2 liter separatory funnel and washed three times with water. The organic phase is then concentrated in a rotary flash evaporator until no additional solvent is removed. The crude product is diluted with methylene chloride and transferred to a separatory funnel. The product is washed three times with 10% HCl. Emulsification of the organic and aqueous phases occurs and requires the addition of small amounts of brine to effect phase separations. The organic phase is then washed with $Ca(OH)_2$ in water. Insoluble calcium oleate salts are removed from the system by suction filtration through a packed Celite bed and the organic phase washed with neutral brine.

The organic phase is then dried over $MgSO_4$ and the desiccant removed by suction filtration. The product is isolated by concentrating it in a rotary flash evaporator at 70° C. (158° F.) until no additional solvent is removed. Yield of the product is 86.6%.

The product is a transparent light amber oil with a mild odor reminiscent of leather. It has a low viscosity.

(b) Food compositions according to the present invention

Low calorie fat-containing food compositions are prepared by using the propoxylated sucrose polyesters prepared as described in Example 1 in the following formulations:

|   | Ingredients | % by weight |
|---|---|---|
|   | Example I - Salad Oils | |
| (A) | Refined, bleached, and lightly hydrogenated soybean oil | 50 |
|   | Propoxylated sucrose polyesters | 50 |
|   | | 100 |
| (B) | Refined cottonseed oil | 90 |
|   | Propoxylated sucrose polyesters | 10 |
|   | | 100 |
| (C) | Propoxylated sucrose polyesters | 100 |
|   | Example II - Plastic Shortening | |
| (A) | Lightly hydrogenated soybean oil (I.V. 107) | 50 |
|   | Propoxylated sucrose polyesters | 40 |
|   | Tristearin (hardstock, I.V. 8) | 10 |
|   | | 100 |
| (B) | 50/50 mixture of hardened cottonseed oil and lard | 40 |
|   | Monoglycerides of soybean oil | 10 |
|   | Propoxylated sucrose polyesters | 50 |

|   | Ingredients | % by weight |
|---|---|---|
|   | | 100 |
| (C) | Propoxylated sucrose polyesters | 100 |
|   | Example III - Prepared Cake Mix | |
| (A) | Specific | |
|   | Cake flour | 36 |
|   | Sugar | 44 |
|   | Shortening (propoxylated sucrose polyesters) | 13 |
|   | Nonfat dried milk solids | 4 |
|   | Leavening | 2 |
|   | Salt | 1 |
|   | | 100 |
| (B) | General | |
|   | Sugar | 35–50 |
|   | Flour | 25–50 |
|   | Shortening (propoxylated sucrose polyesters) | 5–30 |
|   | Leavening | 1–4 |
|   | Cocoa | 0–7 |
|   | Egg | 0–5 |
|   | Milk solids | 0–5 |
|   | Flavor | 0–5 |
|   | | 100 |
|   | Example IV - Prepared Icing Mix | |
|   | Shortening (50/50 mixture of conventional vegetable shortening and propoxylated sucrose polyesters) | 20 |
|   | Salt | 2 |
|   | Nonfat dry milk solid | 5 |
|   | Sugar | 73 |
|   | | 100 |
|   | Example V - Mayonnaise | |
|   | Fat (75:25 blend of propoxylated sucrose polyesters and refined cottonseed oil) | 75 |
|   | Vinegar | 10 |
|   | Egg yolk | 9 |
|   | Sugar | 3 |
|   | Salt | 1 |
|   | Mustard | 1 |
|   | Flavor | 1 |
|   | | 100 |
|   | Example VI - Salad Dressing | |
|   | Fat (propoxylated sucrose polyesters) | 50 |
|   | Cornstarch | 5 |
|   | Vinegar | 10 |
|   | Water | 35 |
|   | | 100 |
|   | Example VII - Margarine | |
|   | Oil (propoxylated sucrose polyesters) | 80 |
|   | Milk solids | 2 |
|   | Salt | 2 |
|   | Monoglyceride | 15 |
|   | Water | 1 |
|   | | 100 |

(c) Synthesis of the oleoyl chloride reactant

Following is the preferred method for synthesizing the oleoyl chloride used in making the product of Example 1.

Oleic acid (141 g, 0.50 mole) is dissolved in methanol (250 ml) in a 2 liter Erlenmeyer flask and potassium hydroxide pellets (28.2 g, 0.50 mole) added. The mixture is then stirred while the pellets gradually dissolve. After four to five hours, reagent grade acetone (1 liter) is slowly added to the solution and a white precipitate formed. The flask is then stoppered and stored in a freezer overnight. The following day the potassium oleate precipitate is collected by suction filtration and washed on the filter with additional acetone. The potassium oleate is then dried at first in a forced air oven at 50° C. (122° F.) and finally in a vacuum oven at 45° C. (113° F.). Yield of potassium oleate is in the 80 to 90 percent range, about 140 g per batch.

A 5 liter, three-neck round bottom flask is equipped with a refluxing condenser, a magnetic stirrer, a 250 ml cylindrical funnel, and an argon purge. The flask is charged with dry potassium oleate (230 g, 0.72 mole) slurried in 1 to methylene chloride - hexane (2.5 liters) and a few crystals of KCl added to the flask. The flask is then purged with argon gas and kept under a positive head of argon. The entire contents of an ampule of oxalyl chloride (100 g, 0.79 mole) is diluted with methylene chloride (100 ml) and poured into the cylindrical funnel. The oxalyl chloride solution is added dropwise to the slurry with gentle stirring over a 2 to 3 hour period with substantial evolution of $CO_2$ and CO occurring. During the addition the potassium oleate gradually disappears and is replaced by a finer precipitate of KCl. The reaction miXlure is allowed to stand under argon with no further agitation overnight. The following day the KCl precipitate is removed from the product solution by suction filtration through a bed of Celite (diatomaceous earth). The filtered solution is then concentrated by rotary flash evaporation until no additional solvent is removed from the product. The product is stored in sealed bottles under argon until used. The oleoyl chloride prepared is a pale yellow oil with a pungent odor. Yield of this reaction is about 90 percent. Confirmation of the product,s identity is made by infrared spectroscopy.

What is claimed is:

1. A fat substitute comprising a fatty acid ester of an alkoxylated polyol, wherein:
    (a) the polyol is selected from the group consisting of sugars and sugar alcohols, and mixtures thereof, and wherein the sugars and sugar alcohols contain at least 4 hydroxyl groups;
    (b) between 1 and about 50 alkoxyl groups are attached by ether linkages to each polyol molecule;
    (c) each alkoxylated polyol is esterified with between about 6 and about 8 fatty acid groups;
    (d) the fatty acids contain between about 2 and about 24 carbon atoms; and
    (e) the alkoxyl group is derived from ethylene oxide.

2. A fat substitute according to claim 1 wherein the polyol is sucrose.

3. A fat substitute according to claims 1 wherein between about 8 and about 32 alkoxyl groups are attached to each polyol molecule.

4. A fat substitute according to claims 1 wherein each alkoxylated polyol is esterified with about 8 fatty acid grups.

5. A fat substitute according to cliams 1 wherein the fatty acids contain between about 8 and about 22 carbon atoms.

6. A fat substitute according to claims 1 wherein between about 1 and about 4 alkoxyl gruops are attached by ether linkages to each attachment site of the polyol molecule.

7. A low calorie fat-containing food compositions which comprises non-fat ingredients and fat ingredients, from about 10% to about 100% by weight of said fat ingredients consisting essentially of a fatty acid ester of an alkoxylated polyol, wherein:
    (a) the polyol is selected from the group consisting of sugars and sugar alcohols, and mixtures thereof, and wherein the sugars and sugar alcohols contain at least 4 hydroxyl groups;
    (b) between 1 and about 50 alkoxyl groups are attached by ether linkages to each polyol molecule;
    (c) each alkoxylated polyol is esterified with between about 6 and about 8 fatty acid groups;
    (d) the fatty acids contain between about 2 and about 24 carbon atoms; and
    (e) the alkoxyl group is derived from ethylene oxide.

8. A food composition according to claim 7 wherein the polyol is sucrose.

9. A food composition according to claims 7 wherein between about 8 and about 32 alkoxyl groups are attached to each polyol molecule.

10. A food composition according to claims 7 wherein each alkoxylated polyol is esterified with about 8 fatty acid groups.

11. A food composition according to claims 7 wherein the fatty acids contain between about 8 and about 22 carbon atoms.

12. A food composition according to claims 7 wherein between about 1 and about 4 alkoxyl groups are attached by ether linkages to each attachment site of the polyol molecule.

* * * * *